(12) United States Patent
Schmid et al.

(10) Patent No.: US 10,568,181 B2
(45) Date of Patent: Feb. 18, 2020

(54) SURGICAL LIGHT AND METHOD FOR OPERATING A SURGICAL LIGHT

(71) Applicant: TRUMPF MEDIZIN SYSTEME GMBH + CO. KG, Saalfeld (DE)

(72) Inventors: Michael Schmid, Grobenzell (DE); Mathias Frenzel, Germering (DE)

(73) Assignee: TRUMPF MEDIZIN SYSTEME GMBH + CO. KG, Saalfeld (DE)

(*) Notice: Subject to any disclaimer, the term of this patent is extended or adjusted under 35 U.S.C. 154(b) by 267 days.

(21) Appl. No.: 15/524,692

(22) PCT Filed: Oct. 28, 2015

(86) PCT No.: PCT/EP2015/074995
§ 371 (c)(1),
(2) Date: May 5, 2017

(87) PCT Pub. No.: WO2016/071178
PCT Pub. Date: May 12, 2016

(65) Prior Publication Data
US 2017/0325319 A1 Nov. 9, 2017

(30) Foreign Application Priority Data
Nov. 7, 2014 (DE) .......... 10 2014 222 793

(51) Int. Cl.
*H05B 37/02* (2006.01)
*H05B 33/08* (2020.01)
(Continued)

(52) U.S. Cl.
CPC ......... *H05B 37/0227* (2013.01); *A61B 90/35* (2016.02); *H05B 33/0803* (2013.01); *H05B 35/00* (2013.01); *F21W 2131/20* (2013.01)

(58) Field of Classification Search
CPC .... H05B 37/0227; H05B 35/00; A61B 90/35; F21V 14/00; F21V 14/003; F21V 23/003;
(Continued)

(56) References Cited

U.S. PATENT DOCUMENTS 3,870,877 A * 3/1975 Tolbird ................. H03K 17/79
250/208.4
4,158,132 A * 6/1979 O'Dell ................. H05B 37/029
250/205

(Continued)

FOREIGN PATENT DOCUMENTS

DE 102005009228 A1 4/2007
EP 1722157 11/2006
(Continued)

OTHER PUBLICATIONS

English Translation of the International Preliminary Report on Patentability dated May 18, 2017.
(Continued)

*Primary Examiner* — Jong-Suk (James) Lee
*Assistant Examiner* — Christopher E Dunay
(74) *Attorney, Agent, or Firm* — Barnes & Thornburg LLP

(57) ABSTRACT

A surgical lamp and a method for illuminating a surgical field on a human body by the surgical lamp are provided. The surgical lamp comprises a lamp body (1), a control device (4) and at least one separate function module (6, 7). The lamp body (1) comprises at least one illuminant (3) for illuminating the surgical field and at least one interface having a first fixation device (11), a power supply terminal (12) and/or a data connection device (13). The control device (4) is provided for controlling the at least one illuminant (3) and is connected to the data connection device (13) of the at least one first interface for data transmission.

(Continued)

The at least one function module (6, 7) comprises a second interface, having a second fixation device (14), a second power supply terminal (15) and/or a second data connection device (16), being compatible to the first interface and that can be docked thereto. Further, the lamp body (1) comprises a recognition device for recognizing a type of a docked function module (6, 7) and the control device (4) is configured to control the at least one illuminant (3) depending on the type of the docked function module (6, 7).

19 Claims, 2 Drawing Sheets

(51) Int. Cl.
   *H05B 35/00* (2006.01)
   *A61B 90/35* (2016.01)
   *F21W 131/20* (2006.01)
(58) Field of Classification Search
   CPC ........ F21V 23/006; F21V 23/06; F21S 2/005; F21S 2/00
   See application file for complete search history.

(56) References Cited

U.S. PATENT DOCUMENTS

| | | | | |
|---|---|---|---|---|
| 4,884,008 | A * | 11/1989 | Bossler | F21V 14/04 315/152 |
| 5,999,952 | A * | 12/1999 | Jenkins | G06F 1/16 361/679.21 |
| 8,967,831 | B2 * | 3/2015 | Chien | F21V 3/02 362/276 |
| 9,035,555 | B2 * | 5/2015 | Fornasiero | A61B 90/35 315/129 |
| 10,047,940 | B2 * | 8/2018 | Grunzweig | A63H 33/046 |
| 10,215,351 | B2 * | 2/2019 | Spiro | F21S 8/086 |
| 2004/0129860 | A1 | 7/2004 | Thibaud et al. | |
| 2005/0195599 | A1 | 9/2005 | Marka | |
| 2006/0193125 | A1 | 8/2006 | Fluss | |
| 2006/0291204 | A1 | 12/2006 | Marka et al. | |
| 2007/0138966 | A1 | 6/2007 | Marka | |
| 2008/0285820 | A1 | 11/2008 | Voelker | |
| 2010/0243823 | A1 | 9/2010 | Hardy et al. | |
| 2010/0244692 | A1 * | 9/2010 | Van Endert | F21S 2/005 315/32 |
| 2010/0315210 | A1 * | 12/2010 | Travis | G06F 1/1632 340/538 |
| 2011/0013395 | A1 * | 1/2011 | Melzner | F21S 2/005 362/240 |
| 2013/0113909 | A1 * | 5/2013 | DeLand | A61B 50/28 348/77 |
| 2013/0310652 | A1 * | 11/2013 | Barsoum | A61B 90/30 600/249 |
| 2014/0292225 | A1 * | 10/2014 | Arbinger | H05B 37/0218 315/294 |
| 2016/0310861 | A1 * | 10/2016 | Hirata | A63F 13/327 |
| 2017/0367785 | A1 * | 12/2017 | Munari | H05B 33/0854 |
| 2019/0060026 | A1 * | 2/2019 | Geerlings | A61B 90/30 |

FOREIGN PATENT DOCUMENTS

| | | |
|---|---|---|
| EP | 1785665 | 5/2007 |
| JE | 102005044237 A1 | 3/2007 |
| JE | 202007007054 U1 | 8/2007 |

OTHER PUBLICATIONS

PCT Search Report and Written Opinion for PCT/EP2015/074995, completed Feb. 26, 2016.

* cited by examiner

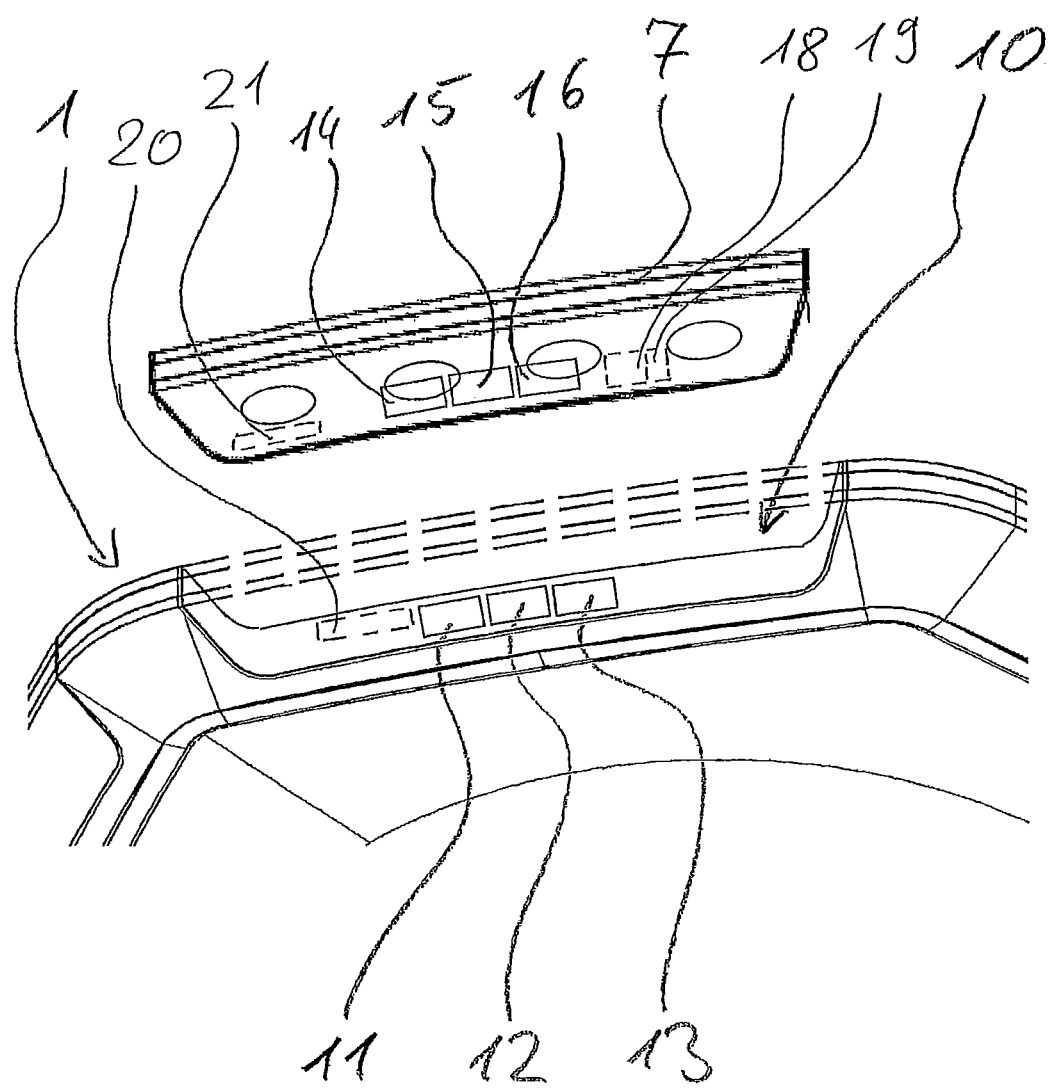

SURGICAL LIGHT AND METHOD FOR OPERATING A SURGICAL LIGHT

CROSS REFERENCES TO RELATED APPLICATIONS

This application is a U.S. national phase of PCT/EP2015/074995, filed on Oct. 28, 2015, which claims the benefit of and priority to German Patent Application Serial No. 102014222793.3, filed on Nov. 7, 2014, both of which are incorporated herein by this reference in their entirety.

The invention relates to a surgical lamp and method for operating a surgical lamp, in particular, a surgical lamp having additional functionalities, and a method for illuminating a surgical field on a human body by this surgical lamp.

Surgical lamps comprising additional functionalities besides the illumination of the surgical filed are known. Surgical lamps are e.g. equipped with camera system which can be docked. Attaching a camera e.g. at a lamp body of the surgical lamp is recognized by the surgical lamp. The camera is supplied with electric power and it can be controlled by operating elements of the surgical lamp. For example, the camera can be rotated for an alignment of the image or the image section can be down-sized or enlarged by a zoom function.

A surgical lamp in which a color temperature of the emitted light can be adjusted is further known from document DE 20 2007 007 054 U1. The information about the color temperature of the set light is passed to the camera at the surgical lamp by the control device of the surgical lamp so that a white balance of the camera can be executed by means of the color temperature information.

Document EP 1 785 665 A1 shows a surgical lamp in which the lighting modules of the lamp body can be replaced. Concerning the color temperature and the intensity of the emitted light, the lighting modules are factory-calibrated for various operating modes, wherein calibration values are stored in the lighting modules. These calibration values are retrieved from the lighting modules by a central control device and the lighting modules are operated according to their calibration values by the central control device.

Therefore, surgical lamps comprising function modules, i.e. modules executing a specific function and which can be docked to the surgical lamp, and comprising data connections to the function modules so that these function modules are operated according to their characteristics and function possibilities are known.

However, if a specific function module by which not only the operation of the specific function module but the operation of the entire lamp is affected is operated in connection with the surgical lamp, the surgical lamp has to be adapted for the fixation of the function module and for its control by the surgical lamp by a service-sided intervention.

The object underlying the invention is to create a surgical lamp which can be adapted to the operation of specific function modules affecting the operation of the surgical lamp in a flexible manner without large efforts.

The object is achieved by a surgical lamp according to claim 1 and a method according to claim 14.

By provision of an interface at a lamp body of a surgical lamp and at a separate function module and by adaption of a control device of the surgical lamp so that the lamp body with its illuminants and, as the case may be, further function elements are operated according to stored operating data retrieved from the separate function module, it is possible to adapt the surgical lamp to the operation of specific subsequently provided function modules without service-sided interventions.

The invention is elucidated by means of embodiments referring to the attached drawings.

In particular:

FIG. 2 shows an enlarged section of the lamp body of FIG. 1 with one of the separate function modules and a recess therefore, and a schematic illustration of the first and second interfaces.

FIG. 1 shows a lamp body 1 of a surgical lamp. The lamp body is fixed to e.g. a room ceiling by a suspension device (not shown) via a pivot joint 2 so that it can be pivoted in all directions.

Figure 1:
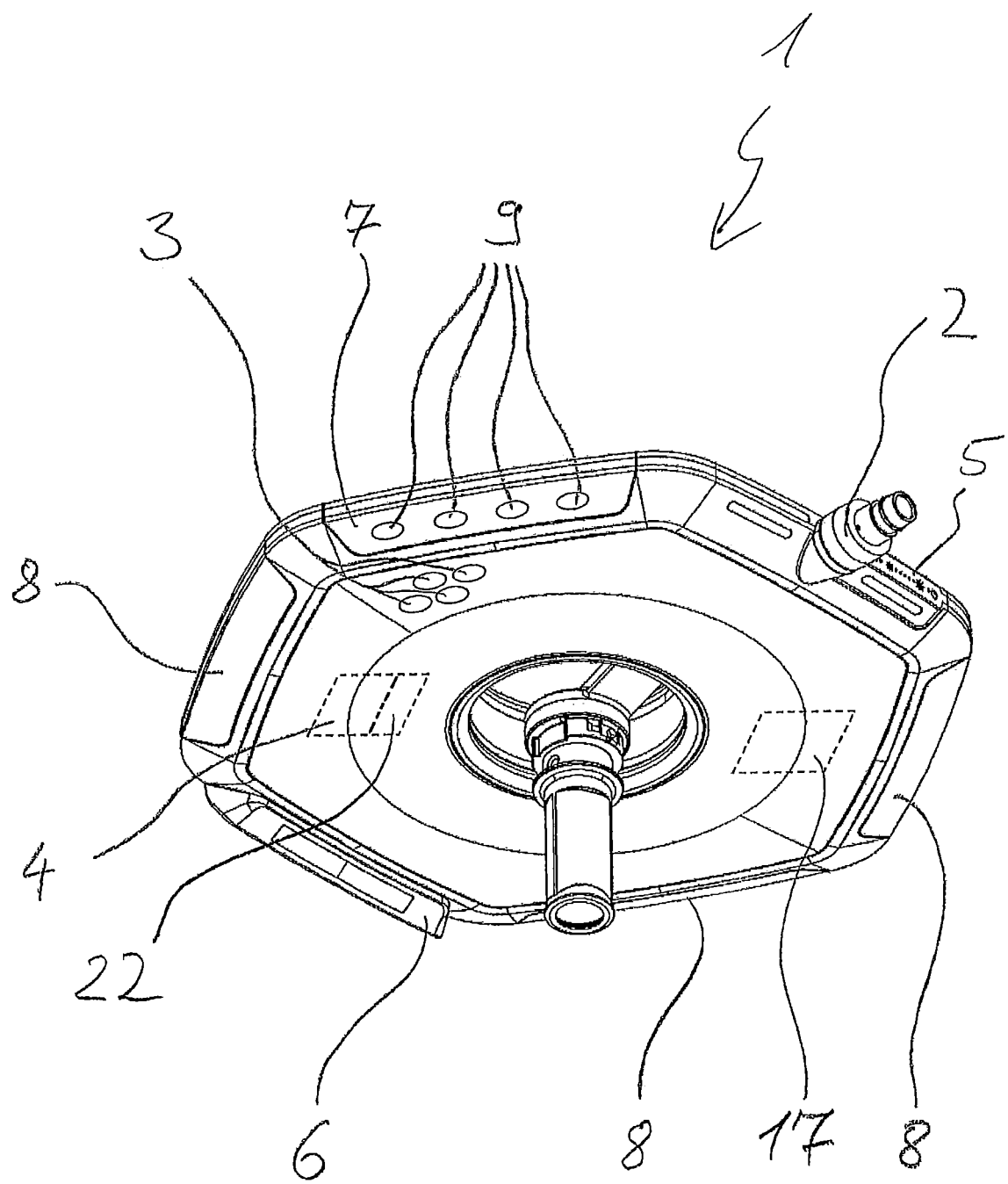
FIG. 1 shows a lamp body of a surgical lamp having separate function modules.

The lamp body 1 is provided with several illuminants 3. The illuminants 3 are located within the lamp body 1 and, in the alignment of the lamp body 1 shown in FIG. 1, they radiate light downwardly in order to illuminate a surgical field on a human body. Only four of a plurality of the illuminants 3 are illustrated here. Here, the illuminants 3 are carried out as LEDs and they are basically distributed across an entire light escape area at the lamp body 1. Alternatively, at least one single illuminant is provided.

The surgical lamp further comprises a control device 4 in the lamp body 1 or, alternatively, at another suitable location, e.g. at a ceiling fixation.

The control device 4 comprises a memory area 22 in which the operating data are stored. In particular, later described illumination scenarios can optionally be stored therein.

Here, at the lamp body 1, the surgical lamp is provided with operating elements 5, wherein the operating elements 5 can also be provided at the suspension device or at a wall panel (not shown).

Both, the illuminants 3 and the operating elements 5 are connected to the control device 4. The control device 4 controls the illuminants 3 according to settings at the operating elements 5. By the operating elements 5, setting of an intensity of the light radiated from the illuminants 3, i.e. a brightness in the surgical field, as well as of a diameter of a light field generated by the illuminants 3 in the surgical field are possible. Optionally, further setting possibilities, e.g. a color temperature of the radiated light, is possible.

The lamp body 1 is provided with separate function modules 6, 7 at two docking points. Here, the function modules 6, 7 are arranged at the outer area, i.e. at the periphery of the lamp body 1. Alternatively, according to the function, the function modules 6, 7 can also be provided at another location at the lamp body, e.g. on the topside or in the light escape area.

However, the lamp body 1 is yet provided with further docking points having recesses 10 (see FIG. 2) which are to be covered by covers 8 in order not to deteriorate the hygienic conditions if no function modules 6, 7 are attached. In particular, thus, an aerodynamic shape of the lamp body 1 is enabled even though no function modules 6, 7 are attached to the lamp body 1. Thus, a flow field of a ventilation ceiling above the surgical site is scarcely impaired.

Here, the function module 6 is a sensor module by which the distance between the lamp body 1 and the surgical field can be measured. The sensor module 6 is connected to the control device 4 and transmits detected data to the control device 4 which, based on that, e.g. adjusts or maintains a light field diameter or a brightness constant.

Here, the function module 7 is a lighting module. In the lighting module 7, further illuminants 9 are provided. The illuminants 9 in the lighting module 7 change the photometric characteristics of the surgical lamp. In the lighting module 7, further illuminants 9 being comparable with the illuminants 3 within the lamp body 1 in view of their photometric characteristics, e.g. a color temperature or an intensity of the radiated light, are provided. Therewith, it is possible to increase the intensity of the radiated light while adhering the requirements according to the standard. Furthermore, it is alternatively possible to e.g. enlarge the light field diameter. Optionally, an enhanced shadow management, i.e. an underlighting of obstacles or fading of shadow-generating illuminants, is provided.

Alternatively, also other or specific illuminants 9 having other photometric characteristics can be provided in order to be able e.g. to execute fluorescence diagnostics or to set another color temperature of the radiated light.

In further alternatives, also e.g. camera modules or sensor modules as function modules are possible. In one embodiment, a single function module is provided, however, also several function modules can be provided. Furthermore, combinations of functions, as e.g. an integration of illuminants and sensors in a function module, are possible.

The function modules are shaped such that they are essentially adapted to a basic shape of lamp body in order not to impair the aerodynamic shape of the lamp body.

In FIG. 2, an enlarged section of the lamp body 1 having a recess 10 for one of the separate function modules 6, 7 and a schematized illustration of the first and second inter face are shown.

The recess 10 is also shown in a merely schematized manner. Basically, the recess 10 offers one of the docking points and space for docking a function module 6, 7.

In the recess 10 at the lamp body 1, therefore, at the outer area of the lamp body 1, a first interface comprising a first fixation device 11, a first power supply terminal 12, and a first data connection device 13, being schematized shown here, is provided. The power supply terminal 12 can optionally also be integrated in the data connection device 13. Here, in the lamp body 1, five identical first interfaces are provided in the outer area of the lamp body 1. Alternatively, only one first interface or another number can be provided. The first interfaces are respectively identically carried out so that a standard interface is formed.

The function module 7 comprises, being also schematically shown, a second interface consisting of a second fixation device 14, a second power supply terminal 15, and a second data connection device 16. The second interface at the function module can be connected to the first interface at the lamp body 1 and it is compatible thereto.

The first fixation device 11 and the second fixation device 14 fix the function module 6, 7 to the lamp body 1. They are optionally developed such that the first and second interfaces can be connected and separated by hand, i.e. without a tool, in order to render the assembly and disassembly as simply as possible. For safety purposes, a locking device, releasable by hand, of the fixation device 11, 14 is optionally provided. Alternatively, the assembly or disassembly is also only possible by means of a tool in order to prevent unauthorized assembly or disassembly.

The first power supply terminal 12 is connected to a power supply unit 17 of the surgical lamp. Via the first power supply terminal 12 or, optionally, via the first data connection device 13 which is then connected to the power supply unit 17, and the second power supply terminal 15 or, optionally, the second data connection device 16 at the function module 6, 7, this is supplied with power.

The first data connection device 13 at the lamp body 1 is connected to the control device 4. The second data connection device 16 at the function module 6, 7 is connected to a memory element 18 in the function module 6, 7. Optionally, the control device 19 for controlling the function module is also provided therein. The connection can be respectively made by wire or, alternatively, also wireless, e.g. via radio.

In an alternative embodiment, the first and/or second interfaces can also be designed differently.

If e.g. first function modules 6, 7 are envisaged to be docked only to predetermined positions at the lamp body 1, the first interfaces can be formed accordingly so that only the first function modules 6, 7 having a certain characteristic of the second interface can be docked at predetermined positions at the lamp body 1. The first interface and the second interface are then coded e.g. by a protrusion on one of the first or second interface, e.g. at a predetermined position or having a predetermined shape, and a recess complementary thereto in the other of the first or the second interface. Further possibilities for coding are specific characteristics, as e.g. the shape or the position of the first and second fixation devices 11, 14 of the first and second power supply terminals 12, 14 or of the first and second data connection devices 13, 16.

If others than the first function modules 6, 7 are envisaged to be docked at other predetermined positions or at all of the positions, the respective first and second interfaces are accordingly coded, e.g. as described above.

In the lamp body 1, a device by which a type of the docked function module 6, 7 can be recognized is provided. The type is e.g. recognized by evaluating specific signals from the function module 6, 7 by the control device 4. Alternatively, switches or sensors recognizing specific features, e.g. protrusions, of different types of function modules 6, 7 are provided. The control device 4 controls the illuminants 3 in the lamp body 1 and, as the case may be, the function module 6, 7 according to its type.

In the lamp body 1, a switching device 20 for the first power supply terminal 12 and/or the first a data connection device 13 is respectively optionally provided for one of the first interfaces. In the switched on-state, the switching device 20 connects the first power supply terminal 12 to the power supply unit 17 and the first data connection device 13 to the control device 4 of the surgical lamp and interrupts the connections in a switched off-state.

If the lamp body 1 is provided with the optional switching devices 20, the function modules 6, 7 are respectively provided with an activation device 21. The activation device 21 switches on the switching device 20 arranged at the recess 10 if the function module 6, 7 is fixed to the lamp body 1 in the respective recess 10 via the first interface and the second interface. When the respective function module 6, 7 is separated from the lamp body 1, i.e. not yet fixed, the connections between the first power supply terminal 12 and the power supply unit 17 and between the first data connection device 13 and the control device 4 of the surgical lamp are separated.

Here, the switching device 20 is a reed contact in the lamp body 1 and the activation device 21 is a magnet, switching the reed contact, in the function module 6, 7. Alternatively, also other switching or activation devices, as e.g. a mechanically operable switch at the lamp body 1 and a switching face at the function module 6, 7, are possible.

In an alternative embodiment, a separate switch connecting the first power supply terminal 12 to the power supply unit 17 and the first data connection device 13 to the control device 4 of the surgical lamp and interrupting it in a switched off-state is provided. The separate switch is switchable either manually or by the control device 4.

In the memory element 18 of the function module 6, 7, operating data of the function module 6, 7 are stored. In the case of a lighting module 7, the operating data are operating data as calibration data of the illuminants 9. Optionally, also an operating software can be stored in the memory area. Further, illumination scenarios executable by the function module can optionally also be stored in the memory element 18.

In alternative embodiments, the operating elements 5 are carried out as adaptable user interface. The user interface automatically adapts to the configuration of the surgical lamp having the function modules and only displays the lamp body 1 with the existing function modules 6, 7. In one of the embodiments, the user interface shows a maximum configuration, wherein functionalities of the surgical lamp including the function modules are locked or activated depending on the actual configuration.

In operation, upon attaching one of the separate function modules 6, 7 to one of the recesses 10 at the lamp body 1, the respective first fixation device 11 is connected to the second fixation device 14 and, optionally via the switched on switching device 20, the respective first power supply terminal 12 as well as the respective first connection device 13 are connected to the second power supply terminal 15 and to the second data connection device 16 of the second interface of the function module 6, 7. The control device recognizes, by means of the recognition device for recognizing the type of the function module, the type thereof. Depending on the type of the function module, the control device 4 then controls the illuminants 3 in the lamp body 1. Optionally, the function module 6, 7 is also controlled according to its type by the control device 4. If illumination scenarios for this type of the function module 6, 7 are included in the memory area 22 of the control device 4, the illuminants 3 and, in the case of the docked lighting module 7 also its illuminants 9, are controlled according to the stored illumination scenario.

Optionally, the control device 4 sends an electronic query to the memory element 18 of the function module 6, 7, whereupon, as the case may be, data for recognizing the type of the function module 6, 7 and operating parameters are retrieved by the control device 4 of the surgical lamp. As a further option, the illumination scenarios stored in the memory element 18 are retrieved. The control device 4 controls and operates the illuminants 3 of the lamp body 1 as well as the just docked function module 6, 7 and, as the case may be, further devices of the surgical lamp or further function modules 6, 7 controlled by the control device 4 of the lamp body 1 now based on the operating parameters or the illumination scenarios.

As an option, the illumination scenarios are stored in the control device 4 for controlling the illuminants 3. Therefore, an illumination scenario in which e.g. the maximum intensity of the illuminants 3 within the lamp body 1 is reduced upon attacking an additional lighting module 7 is stored e.g. in connection with the docked lighting module 7. The maximum intensity of the illuminants 3 with in the lamp body 1 and, as the case may be, of the additional lighting modules 7 is reduced so that a maximum admissible illuminance in the surgical field is not exceeded, therefore, the function module as well as the lamp body 1 are controlled according to the operating data stored in the function module.

A further illumination scenario is optionally possible in connection with a docked sensor module 6. The sensor module 6 gives data concerning a position of an obstacle present between the lamp body 1 and the surgical field to the control device 4. In the memory area 22 of the control device 4, an illumination scenario in which the ones of the illuminants 3, in the light ray of which the obstacle is present, are dimmed or switched off in order to prevent or to reduce shadow on the surgical field is stored. Optionally, all or some of the remaining illuminants 3 are operated with increased intensity. In a further optional embodiment, the lamp body 1 is additionally provided with lighting modules 7, the illuminants 9 of which, in a further illumination scenario, are included in this function of the shadow prevention or reduction. Thus, also the additional lighting modules 7 are controlled according to operating data retrieved from another function module 6, 7.

Upon attachment of a function module 6, 7 to the lamp body 1, the functionality of which has not been stored in the control device 4 so, an operating software update according to the operating software stored in the memory element 18 of the function module 6, 7 is performed in the control device 4.

The various embodiments can be combined to one another.

What is claimed is:

1. A surgical lamp, for illuminating a surgical field on a human body, the surgical lamp having
   a lamp body, wherein the lamp body comprises at least one illuminant for illuminating a surgical field and a plurality of first interfaces formed as recesses in the outer surface of the lamp body, wherein each of the plurality of first interfaces has a first fixation device and a data connection device arranged on an inner surface of the recess,
   a control device, the control device connected to the data connection device of the at least one first interface for data transmission, and
   a plurality of interchangeable function modules each having a unique function, wherein each of the function modules comprise a second interface having a second fixation device and a second data connection device that can be docked to one of the first interfaces, and a memory element including data which identifies each unique function module's type,
   wherein, upon connection of a second interface to a first interface, whereby a function module is received and retained within the recess of the first interface, the control device queries the memory device of the function module to identify the type of function module,
   wherein the control device is configured to control the at least one illuminant in the lamp body depending on the type of the docked function module, and
   wherein a cover is provided to cover any unused first interface.

2. The surgical lamp according to claim 1, wherein the first interfaces and the second interfaces are configured such that their connecting and separating is made without tools.

3. The surgical lamp according to claim 1, wherein the control device comprises a memory area, and, in the memory area, various illumination scenarios are stored.

4. The surgical lamp according to claim 3, wherein the plurality of interchangeable function modules comprises at least one lighting module.

5. The surgical lamp according to claim 4, wherein the illumination scenarios comprise data ensuring the adherence of a limit value for a maximum illuminance in the surgical field depending on a kind and/or a number of the at least one lighting module.

6. The surgical lamp according to claim 3, wherein the plurality of interchangeable function modules comprises a sensor module.

7. The surgical lamp according to claim 6, wherein the sensor module is configured to give data concerning a position of an obstacle present between the lamp body and the surgical field to the control device, and an illumination scenario, according to which the at least one illuminant is controlled depending on the position of the obstacle such that the at least one illuminant has a light ray in which the obstacle is located is dimmed or switched off, is stored.

8. The surgical lamp according to claim 7, wherein at least one of the plurality of interchangeable function modules comprise a memory element for storing operating data, and wherein the control device is configured to retrieve the operating data from the memory element of the function module and to control the function module as well as the lamp body according to the retrieved operating data.

9. The surgical lamp according to claim 8, wherein the control device is configured, after connecting one of the first interfaces and one of the second interfaces, to retrieve the operating data from the memory area of the connected function module and to control the surgical lamp according to the retrieved operating data.

10. The surgical lamp according to claim 8, wherein the stored operating data comprise both operating parameter and operating software.

11. The surgical lamp according to claim 10, wherein the control device is configured to recognize whether the function module is connected for the first time to the control device and has a predetermined function not stored in the control device, and to perform an update of the operating software of the control device according to the operating software stored in the function module if the predetermined function is not already stored in the control device.

12. The surgical lamp according to claim 8, wherein the control device is configured to control a certain function module according to operating data retrieved from another than the certain function module.

13. The surgical lamp according to claim 1, wherein the plurality of interchangeable function modules comprises an activation device and the lamp body comprises a switching device switched by the activation device for each first interface so that a power supply terminal of the at least one first interface is connected to a power supply unit when one of the function modules is connected to the lamp body via the first interface and the second interface, and the power supply terminal of the one first interface is separated from the power supply unit when then function module is not fixed to the lamp body via the first interface and the second interface.

14. A method for operating a surgical lamp according to claim 1, the method having the steps:
connecting the second interface of the plurality of interchangeable function modules to one of the first interface of the lamp body;
recognizing a type of the docked function module; and
controlling the at least one illuminant depending on the type of the docked function module.

15. The method according to claim 14, wherein the at least one illuminant is controlled depending on the type of the docked function module according to a stored illumination scenario.

16. The method according to claim 14 having the additional steps:
retrieving operating data from a memory element of the plurality of interchangeable function modules;
controlling the plurality of interchangeable function modules as well as the lamp body according to the retrieved operating data.

17. The method according to claim 16 with the step:
controlling one of the plurality of interchangeable function modules according to the operating data retrieved from one of the other function modules.

18. The method according to claim 16 with the additional step:
controlling one of the function modules according to the operating data retrieved from one of the other function modules.

19. The method according to claim 14 with the additional step:
switching a switching device by means of an activation device and, thereby, connecting a power supply terminal of one of the first interfaces to a power supply unit and connecting a data connection device of one of the first interfaces to the control device.

* * * * *